United States Patent
Furukawa et al.

(10) Patent No.: US 6,699,700 B1
(45) Date of Patent: Mar. 2, 2004

(54) CREATINE AMIDINOHYDROLASE AND PROCESS FOR PRODUCING THE SAME

(75) Inventors: Keisuke Furukawa, Chiba (JP); Toshio Ichikawa, Chiba (JP)

(73) Assignee: Kikkoman Corporation (JP)

( * ) Notice: Subject to any disclaimer, the term of this patent is extended or adjusted under 35 U.S.C. 154(b) by 0 days.

(21) Appl. No.: 09/856,645

(22) PCT Filed: Nov. 25, 1999

(86) PCT No.: PCT/JP99/06583

§ 371 (c)(1),
(2), (4) Date: May 24, 2001

(87) PCT Pub. No.: WO00/31245

PCT Pub. Date: Jun. 2, 2000

(30) Foreign Application Priority Data

Nov. 25, 1998 (JP) .......................................... 10/334252

(51) Int. Cl.⁷ ................................................ C12N 9/78
(52) U.S. Cl. ...................................................... 435/227
(58) Field of Search ......................................... 435/227

(56) References Cited

U.S. PATENT DOCUMENTS

| | | | | |
|---|---|---|---|---|
| 3,806,416 A | * | 4/1974 | Mollering et al. | 195/62 |
| 3,907,644 A | * | 9/1975 | Mollering et al. | 195/99 |
| 3,912,588 A | * | 10/1975 | Mollering et al. | 195/29 |
| 4,039,384 A | * | 8/1977 | Suzuki et al. | 195/62 |
| 4,990,453 A | | 2/1991 | Schumacher et al. | 435/231 |
| 5,451,520 A | | 9/1995 | Furukawa et al. | 435/227 |
| 5,932,466 A | | 8/1999 | Furukawa et al. | 435/227 |
| 6,080,553 A | | 6/2000 | Sogabe et al. | 435/18 |

FOREIGN PATENT DOCUMENTS

| | | |
|---|---|---|
| DE | 19536506 A1 | 4/1996 |
| EP | 291321 | 5/1988 |
| EP | 790303 | 8/1997 |
| JP | 8-89255 | 4/1996 |
| JP | 62091182 A | 4/1997 |
| JP | 9-215494 | 8/1997 |
| JP | 10 174585 | 6/1998 |
| WO | WO 00/31245 | 6/2000 |

OTHER PUBLICATIONS

International Search Report for PCT/JP/06583 dated Feb. 21, 2000.
European Search Report for European Patent Application No. 99 97 2676, dated Feb. 4, 2002.
U.S. patent application Ser. No. 09/869,280, Furukawa et al., filed Jun. 27, 2001.
Supplementary European Search Report, for corresponding European Patent Application No. EP 99 96 1487.8, dated Oct. 7, 2002.
Pending claims for U.S. application No. 09/869,280.

* cited by examiner

*Primary Examiner*—Charles L. Patterson, Jr.
(74) *Attorney, Agent, or Firm*—Finnegan, Henderson, Farabow, Garrett, & Dunner, L.L.P.

(57) ABSTRACT

The present invention relates to a creatine amidinohydrolase having the following physicochemical properties: (a) hydrolyzing 1 mole of creatine to generate 1 mole of sarcosine and 1 mole of urea, (b) having a substrate specificity to creatine, (c) having an optimum pH ranging from 6.0 to 7.0, particularly a pH of about 6.5, (d) having a stable pH ranging from 4.0 to 11.0, (e) having an optimum temperature ranging from 50 to 55° C., and (f) having a molecular weight of approximately 92,000 daltons (as measured by gel filtration); and to a method for producing a creatine amidinohydrolase, which comprises, culturing a microorganism having an ability to produce the creatine amidinohydrolase, and recovering the creatine amidinohydrolase from the obtained culture. The creatine amidinohydrolase of the invention is characterized by being insusceptible to bilirubin when measuring creatinine, since its optimum pH is in the weakly acidic range.

6 Claims, 4 Drawing Sheets

CREATINE AMIDINOHYDROLASE AND PROCESS FOR PRODUCING THE SAME

FIELD OF THE INVENTION

The present invention relates to a creatine amidinohydrolase having an optimum pH in the weakly acidic range, and a method for producing the same.

BACKGROUND OF THE INVENTION

Creatine amidinohydrolase is an enzyme which has a catalytic action of hydrolyzing creatine to generate sarcosine and urea. Creatine amidinohydrolase can be used for measuring the amount of creatine existing in human serum or urine, and so this enzyme can be used as a diagnostic agent for various diseases including renal diseases.

Previously, the optimum pH of creatine amidinohydrolase derived from Alcaligenes (which is described in Japanese Patent No. 2788174; Japanese Patent Application Laid-Open Nos. 7-265074 (1995), 9-215494 (1997), and 10-174585 (1998)) has been reported to be from 7.0 to 9.0. So, in a case where the creatine amidinohydrolase is reacted with serum in the optimum pH range, there are disadvantages such that the creatine amidinohydrolase is so susceptible to bilirubin that a measurement error may occur at the measurement of creatinine, although the reaction with substrate is good.

In contrast, when the reaction with serum is performed around pH6.5, the reaction can effectively be performed without the influence of bilirubin and the measurement error does not occur. And so, a creatine amidinohydrolase having an optimum pH of about 6.5 has been required.

In this situation, the object of the present invention is to provide a creatine amidinohydrolase having an optimum pH in the weakly acidic range, and a method for producing the same.

SUMMARY OF THE INVENTION

After thorough studies to achieve the above object, the present inventors have found a creatine amidinohydrolase having an optimum pH in the weakly acidic range can be obtained by making a modification of a creatine amidinohydrolase gene derived from Alcaligenes (Japanese Patent Application Laid-Open No. 8-89255 (1996)).

Therefore, in one aspect of the present invention, a creatine amidinohydrolase having the following physicochemical properties is provided:

(a) hydrolyzing 1 mole of creatine to generate 1 mole of sarcosine and 1 mole of urea;
(b) having a substrate specificity to creatine;
(c) having an optimum pH ranging from 6.0 to 7.0, particularly pH of about 6.5;
(d) having a stable pH ranging from 4.0 to 11.0;
(e) having an optimum temperature ranging from 50 to 55° C.; and
(f) having a molecular weight of approx. 92,000 daltons (as measured by gel filtration).

In one embodiment, the enzyme of the present invention is a mutant of a creatine amidinohydrolase derived from Alcaligenes. Specifically, the enzyme of the present invention has an amino acid sequence comprising a mutation(s) relative to the amino acid sequence shown in SEQ ID NO: 1. More specifically, the enzyme of the present invention is obtainable from an *Escherichia coli* strain, FERM BP-6580. The term "mutation" as used herein means a deletion, substitution, addition or insertion of at least one amino acid.

In another aspect of the present invention, a method for producing a creatine amidinohydrolase is provided, that comprises: culturing a microorganism having an ability to produce the creatine amidinohydrolase with the above properties; and collecting the creatine amidinohydrolase from the obtained culture.

In one embodiment of the present invention, the microorganism is an *Escherichia coli* strain, FERM BP-6580, or a strain derived from said *Escherichia coli* strain. The term "strain derived from" as used herein means a bacterial strain, which can be isolated from the parent strain treated by a natural mutation or an artificial mutation, having an ability to produce a creatine amidinohydrolase with the above properties.

In addition, the present specification includes part or all of the contents as disclosed in the specification and/or drawings of Japanese Patent Application No. 10-334252 (filed on Nov. 25, 1998), which is a priority document of the present application.

DETAILED DESCRIPTION OF THE INVENTION

The present invention is described in detail below.

The creatine amidinohydrolase of the present invention can be obtained, for example, by the following processes.

First, a recombinant plasmid pUCE100 DNA (Japanese Patent Application Laid-Open No. 8-89255 (1996)), which contains a creatine amidinohydrolase gene derived from an isolated Alcaligenes sp. KS-85 strain, is extracted from *Escherichia coli* JM109 (pUCE100) (FERM BP-4803) using, e.g. QIAGEN (Funakoshi Co., Ltd., Tokyo, Japan), then purified.

The vector DNA used for the present invention is not limited to the above plasmid vector DNA, and examples of such a vector DNA include plasmid vector DNAs, bacteriophage vector DNAs and so on. Specifically, pUC118 (Takara Shuzo Co., Ltd., Kyoto, Japan), pQE (Qiagen, Germany), pBluecsript (Stratagene, USA) etc. can be used.

Any method can be applied to obtain a gene encoding a creatine amidinohydrolase protein, which has an amino acid sequence comprising a mutation (e.g. a deletion, substitution or addition) of one or more amino acids relative to the amino acid sequence shown in SEQ ID NO: 1, and has a creatine amidinohydrolase activity, preferably the protein with a creatine amidinohydrolase activity having an optimum pH in the weakly acidic range. Examples of such methods include: a point mutation, by which the above recombinant plasmid DNA is transformed on a random basis, using a chemical mutagen such as hydroxylamine or nitrous acid or performing PCR; a site-directed mutagenesis, which is a known technique to site-specifically substitute or delete the recombinant plasmid DNA using a commercially available kit; a method where the recombinant plasmid DNA is selectively cleaved and the cleaved DNA is connected after deletion or addition of a selected oligonucleotide; and an oligonucleotide-directed mutagenesis. As a mutation method by genetic engineering, a method described in J. Sambrook et al., *Molecular Cloning A Laboratory Manual* (second ed.), Cold Spring Harbor Laboratory Press, 1989 can be applied.

After the above treatment, the recombinant DNA is purified with a desalting column, QIAGEN (Funakoshi Co., Ltd., Tokyo, Japan) to obtain various types of recombinant DNAs.

Using various types of recombinant DNAs obtained as above, a prokaryote such as bacteria or eukaryotes such as fungi and yeast, e.g. *Escherichia coli* strains such as *Escherichia coli* K12, *Escherichia coli* JM109 (Toyobo Co., Ltd., Osaka, Japan) and XL1-Blue (Funakoshi Co., Ltd., Tokyo, Japan), can be transformed or transducted to obtain transformed or transduced microorganisms, which contain recombinant DNAs having therein different types of creatine amidinohydrolase gene fragments.

With regard to the transformed microorganisms, to obtain a strain producing a creatine amidinohydrolase with the property of interest (having its optimum pH in the weakly acidic range) from the obtained transformants (which contain recombinant plasmid DNAs having different types of mutated creatine amidinohydrolase genes therein), the following method can be applied.

The above-obtained transformants are subjected on a colony basis to a liquid culture on a TY medium (containing 50 μg of Ampicilin and 1 mM IPTG) to inducibly produce various types of creatine amidinohydrolase encoded in recombinant plasmid DNA. After culture, the obtained culture is subjected to an ultrasonic disintegration, and the obtained crude enzyme extract is reacted with 0.1 M creatin in 50 mM phosphate buffer (pH6.0). Also a corresponding wild type protein is extracted by the same process as stated above, and while comparing the obtained measurement result with the result of each of the transformed strains, the transformant of interest is selected.

In order to recover creatine amidinohydrolase exhibiting an optimum pH in the weakly acidic range, from the above-selected transformed or transduced microorganism having an ability to produce creatine amidinohydrolase exhibiting an optimum pH in the weakly acidic range, preferably one belonging to Escherichia, the following procedure can be used.

The above microorganism may be cultured by a common solid culture method, but preferably cultured by a liquid culture method.

An example of the medium, in which the above microorganism is cultured, includes the one obtained by: adding at least one inorganic salt such as potassium dihydrogen phosphate, dipotassium hydrogen phosphate, magnesium sulfate, ferric chloride, ferric sulfate or manganese sulfate to at least one nitrogen source such as yeast extract, peptone, meat extract, corn steep liquor, or the effusion of soybean or wheat koji; and as necessary, further adding therein carbohydrate materials, vitamins and the like.

It is appropriate that the initial pH of the medium is set to pH7.0 to 9.0. And the culture is performed at 30 to 42° C., preferably around 37° C., for 6 to 24 hours by a culture method such as submerged aeration-agitation culture, shake culture, or static culture. After culture, creatine amidinohydrolase can be recovered from the obtained culture by common methods for the collection of enzymes.

For example, cells are separated from the culture by e.g. filtration or centrifugation, and washed. Then, creatine amidinohydrolase is preferably recovered from these cells. To recover creatine amidinohydrolase, the cells may be used as they are, but it is preferable to apply the methods of: destroying the cells using various means such as ultrasonicator, French press and Dynamill; lysing the cell wall of the cells using an enzyme such as lysozyme; and extracting the desired enzyme from the cells using a surfactant such as Triton X-100.

In order to isolate creatine amidinohydrolase from the obtained crude enzyme solution, methods commonly used for the purification of enzymes can be used. For example, an appropriate combination of ammonium sulfate salting-out, organic solvent precipitation, ion exchange chromatography, gel filtration chromatography, adsorption chromatography and electrophoresis is preferable.

The physicochemical properties of the obtained creatine amidinohydrolase are set forth below:

(1) Action

The enzyme hydrolyzes 1 mole of creatine to generate 1 mole of sarcosine and 1 mole of urea (2) Substrate Specificity The enzyme has a substrate specificity to creatine.

(3) Optimum pH

Figure 1:
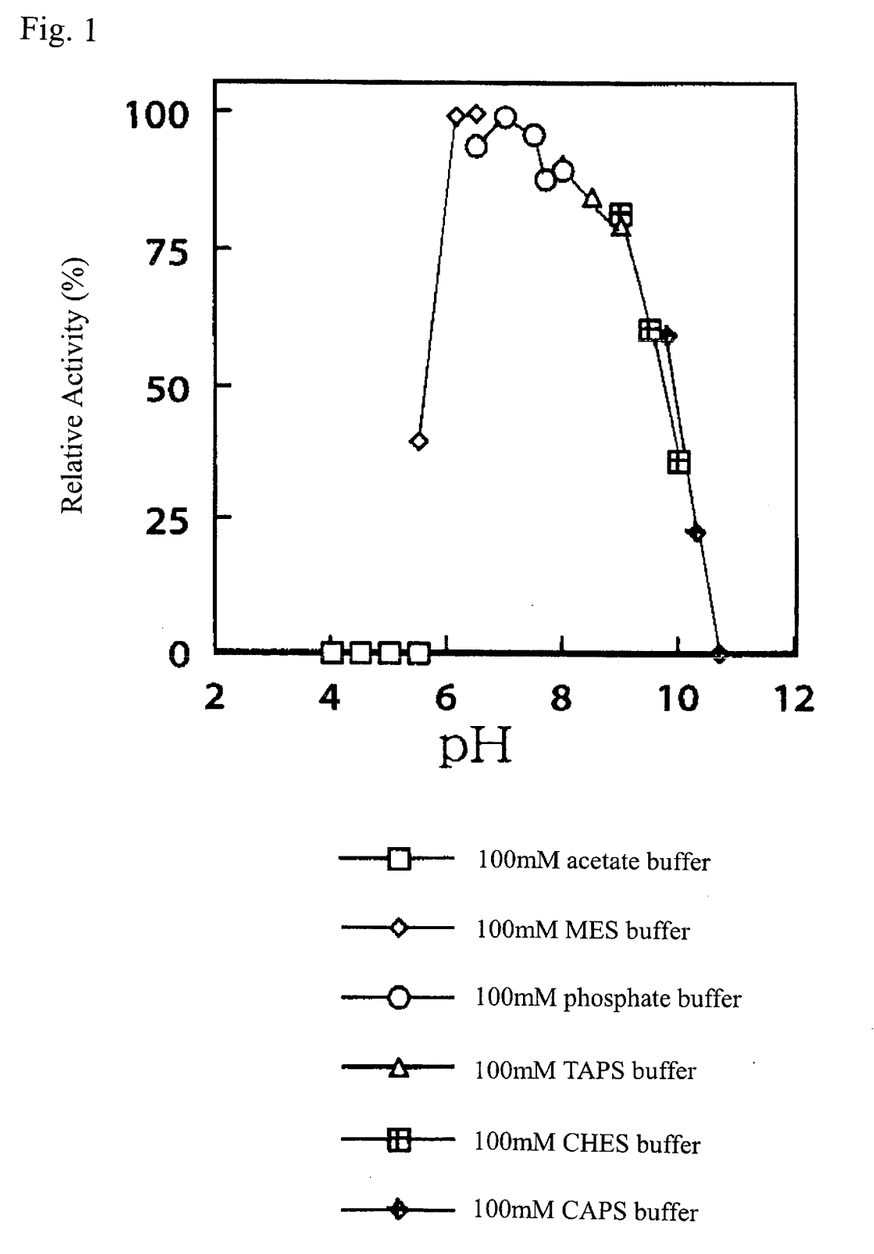
FIG. 1 shows the optimum pH of the enzyme of the present invention.

The enzyme reaction was carried out at 37° C. for 10 minutes under different pH conditions, using, as a buffer, each of 100 mM sodium acetate-acetic acid buffer (pH4.0 to 5.5), 100 mM MES buffer (pH5.5 to 6.5), 100 mM phosphate buffer (pH6.5 to 8.0), 100 mM TAPS buffer (pH8.0 to 9.0), 100 mM CHES buffer (pH9.0 to 10.0) and 100 mM CAPS buffer (pH9.8 to 10.7). The determined relative activity of the enzyme is shown in FIG. 1. The figure shows that the optimum pH of the present enzyme is from pH6.0 to 7.0 in the weakly acidic range, particularly a pH of 6.5 around.

(4) Range of Optimum Temperature

Figure 2:
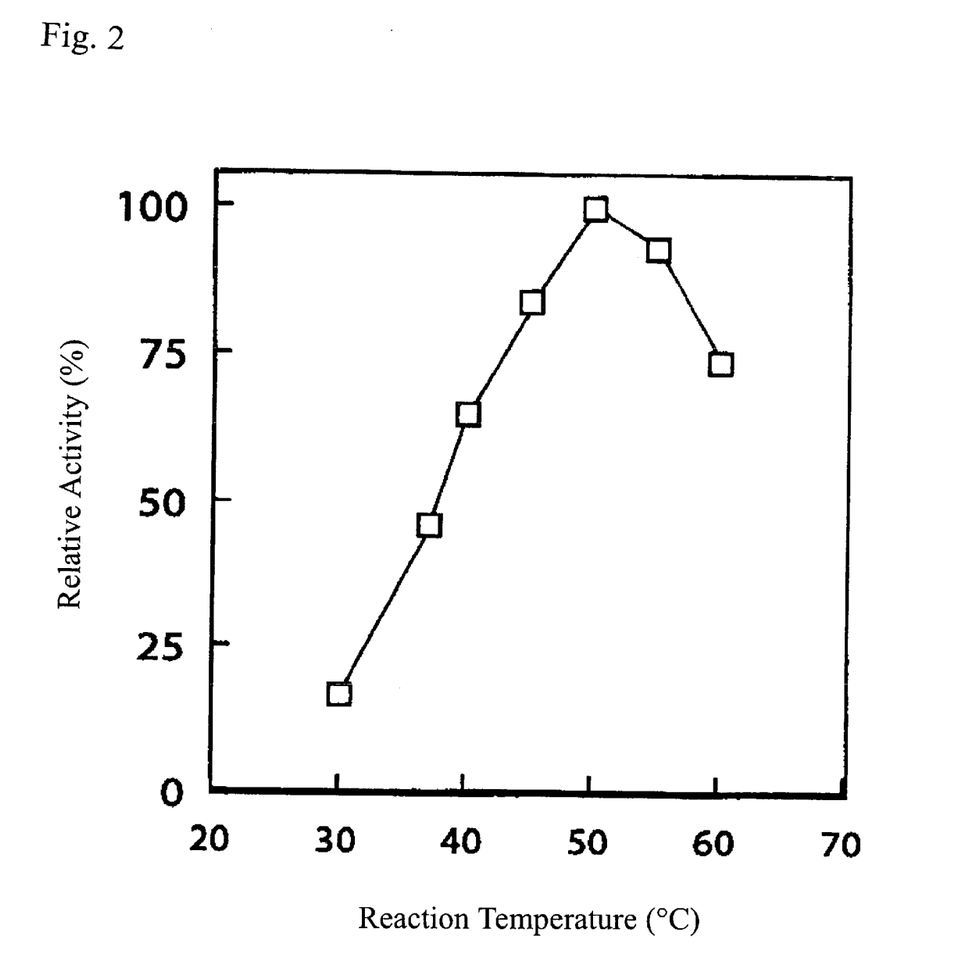
FIG. 2 shows the optimum temperature of the enzyme of the present invention.

Using a reaction solution having of the same composition as the reaction solution for the assay described later, the activity of the present enzyme was measured at different temperatures. The results are shown in FIG. 2. The figure shows that the optimum temperature of the present enzyme ranges from 50 to 55° C.

(5) Range of Stable pH

Figure 3:
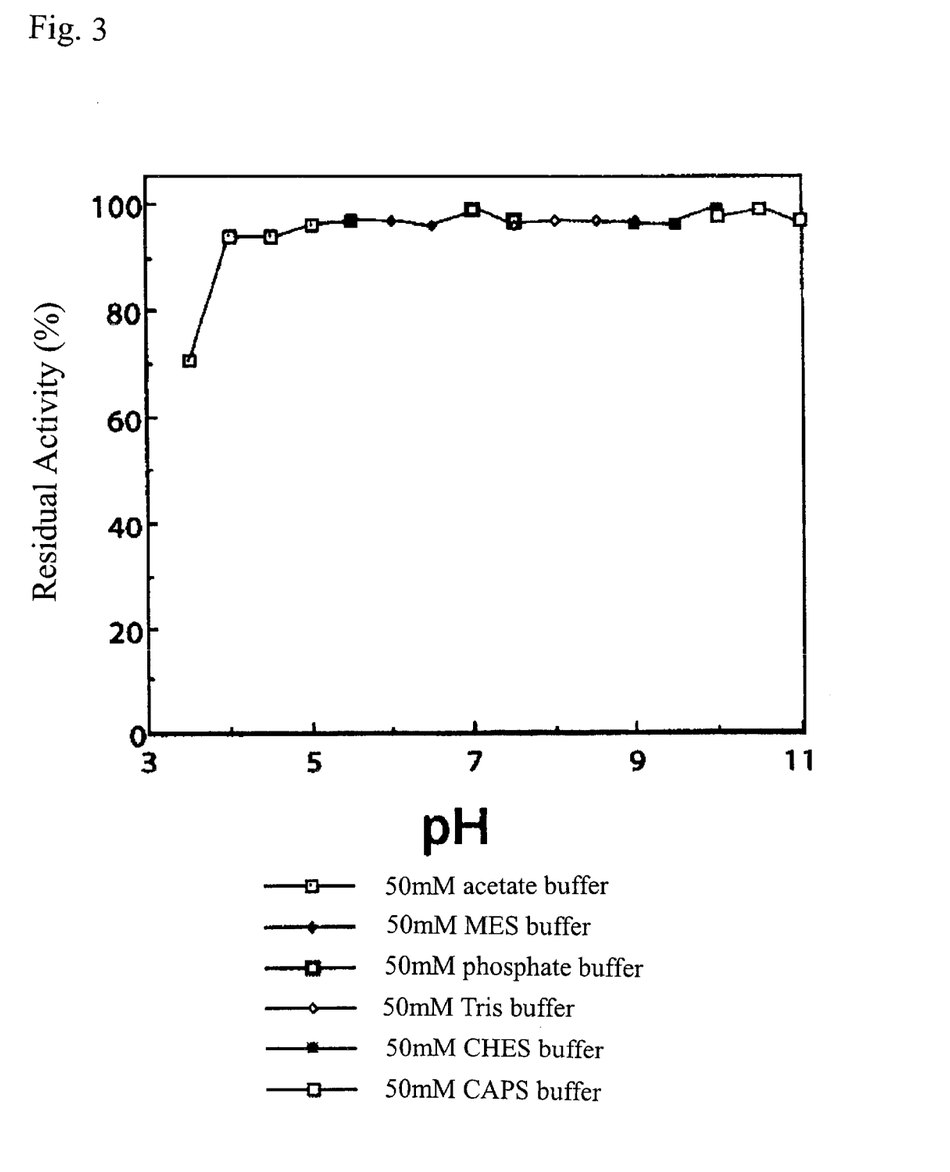
FIG. 3 shows the stable pH range of the enzyme of the present invention.

After treatment of the present enzyme at each of pH4.0 to 11.0 at 25° C. for 16 hours, using as a buffer, each of 50 mM sodium acetate-acetic acid buffer (pH3.5 to 5.5), 50 mM MES buffer (pH5.5 to 7.0), 50 mM phosphate buffer (pH7.0 to 7.5), 50 mM Tris buffer (pH7.5 to 9.0), 50 mM CHES buffer (pH9.0 to 10.0) and 50 mM CAPS buffer (pH10.0 to 11.0), residual activity was measured. The results are shown in FIG. 3. The figure shows that the stable pH of the present enzyme ranges from pH4.0 to 11.0.

(6) Heat Stability

Figure 4:
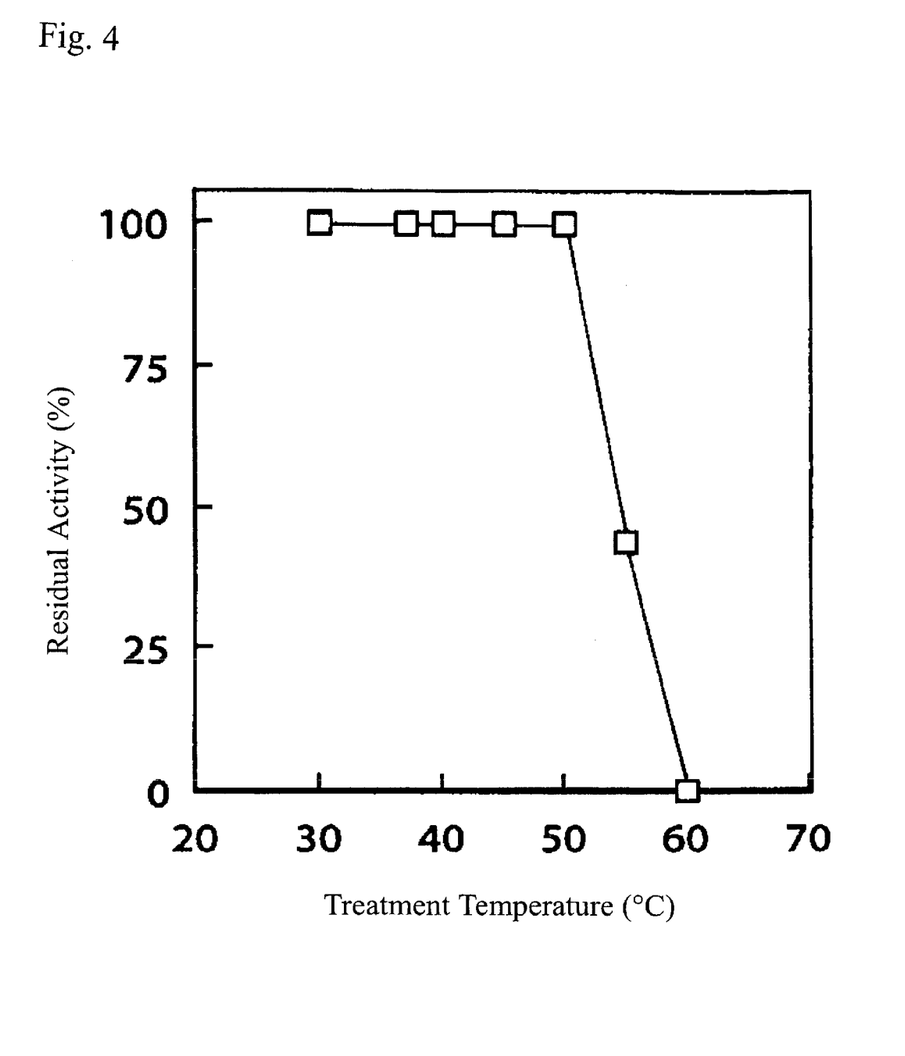
FIG. 4 shows the heat stability of the enzyme of the present invention.

The present enzyme was treated at different temperatures for 30 minutes, using 50 mM Tris-HCl buffer (pH7.5). The results for heat stability are shown in FIG. 4. The figure shows that the present enzyme is stable around 50° C.

(7) Enzyme Assay

The activity of the present enzyme was assayed under the following conditions. Herein, 1 unit (U) is defined as the enzyme activity required to generate 1 μ mole of urea per minute.

(Preparation of Reagent)

Liquid 1: substrate solution 6.63 g of creatine is dissolved in 500 ml of 50 mM phosphate buffer (pH7.7).

Liquid 2: color-development solution 10 g of p-dimethylaminobenzaldehyde is dissolved in 500 ml of special grade ethanol, and then a mixture of 575 ml of resin-treated water and 75 ml of conc. hydrochloric acid is added thereto.

(Measurement Process)
1. 0.9 ml of liquid 1 is subjected to a pre-incubation at 37° C. for 5 minutes.
2. 0.1 ml of an enzyme solution (which is adjusted to about 1 to 2U/ml) is mixed in liquid 1, followed by a reaction at 37° C. for 10 minutes.
3. After reaction, 2 ml of liquid 2 is further mixed therein.
4. The obtained mixture is left at 25° C. for 20 minutes, followed by the measurement of absorbance at 435 nm. The determined value is denoted as $OD_{sample}$.
5. Measurement of a blank value is carried out by the following procedure. After the incubation of 0.9 ml of liquid 1 at 37° C. for 10 minutes, 2ml of liquid 2 is mixed in liquid 1, and 0.1 ml of the enzyme solution is further mixed therein. The obtained mixture is left at 25° C. for 20 minutes, and then absorbance at 435 nm is measured. The determined value is denoted as $OD_{blank}$.

(Calculation of Activity)

$$U/ml = \Delta OD \times 18.06 \times \text{dilution rate}$$

wherein $\Delta OD = OD_{sample} - OD_{blank}$, and the numeral "18.06" represents a coefficient calculated from a urea calibration curve.

(8) Km Value

When the Km value of the present enzyme is measured by the above assay, the Km value for creatine is about 6.0 mM as determined from Lineweaver-Burk plot.

(9) Molecular Weight

The molecular weight of the present enzyme is about 92,000 daltons by gel filtration technique.

The present invention is further described in the following examples. The example is provided for illustrative purposes only, and is not intended to limit the scope of the invention.

EXAMPLE (1) Preparation of Recombinant Plasmid pUCE100 DNA

*Escherichia coli* JM109 (pUCE100) (FERM BP-4803), which comprises DNA encoding a creatine amidinohydrolase having the amino acid sequence shown in SEQ ID NO: 1, was inoculated into 20 ml of TY medium (1% bactotryptone, 0.5% peptone, 0.25% NaCl), and was subjected to shake culture at 37° C. for 18 hours to obtain a culture. The above Escherichia coli strain (accession No. FERM BP-4803) was deposited with the National Institute of Bioscience and Human-Technology, Agency of Industrial Science and Technology (Higashi 1-1-3, Tsukuba-shi, Ibaragi Prefecture, Japan) by the present applicant on Sep. 20, 1994 under the terms of the Budapest Treaty. Cells were collected from this culture by centrifugation at 6,000 rpm for 10 minutes. After that, recombinant plasmid pUCE100 DNA was extracted from the obtained cells using QIAGEN tip-100 (Funakoshi Co., Ltd., Tokyo, Japan) and then purified. Thus, 70 μg of recombinant plasmid pUCE100 DNA was obtained.

(2) Mutagenesis

In accordance with the method of D. M. Morrison (*Method in Enzymology*, 68, 326–331, 1979), 2 μg of the above-obtained recombinant plasmid DNA (100 μg) was transformed into XL1-RED (STRATAGENE, USA), which facilitates the occurrence of mutation by inducing errors in plasmid replication during amplification, and about 1,500 transformed strains were obtained. 500 colonies from among these strains were inoculated into 20ml of TY medium, and subjected to shake culture at 37° C. for 18 hours. After cultivation, cells were collected by centrifugation of the obtained culture at 6,000 rpm for 10 minutes. Plasmid pUCE100 was extracted from the cells using QIAGEN tip-100 (Funakoshi Co., Ltd., Tokyo, Japan), and purified to obtain 70 μg of recombinant plasmid pUCE100 DNA. Using 5 μg of the obtained plasmid, *Escherichia coli* JM109 (Toyobo Co., Ltd., Osaka, Japan) was transformed by the method of D. M. Morrison (*Method in Enzymology*, 68, 326–331, 1979), and transformed strains comprising about 2,000 mutated plasmids were obtained. As a result of performing screening on the transformant in the weakly acidic range according to the method described in (3) below, *Escherichia coli* JM109 (pUCE100TK) producing creatine amidinohydrolase, whose optimum pH shifted to an acidic side, was obtained.

(3) Screening of Mutant Strains With Optimum pH Shifted to the Weakly Acidic Range First, the transformant obtained in (2) above was subjected to a liquid culture on a TY medium (2ml per colony, containing 50 μg of Ampicilin and 1 mM IPTG) to inducibly produce various types of creatine amidinohydrolase encoded in plasmids. After culture, the obtained culture was subjected to ultrasonification, and at pH6.0 and pH7.7, the activity of the obtained crude enzyme extract was measured.

After measurement, the relative activity values at pH6.0 and pH7.7 were calculated. Then, by comparing the relative activity values between mutant creatin amidinohydrolase and wild type creatine amidinohydrolase, which was extracted in the same way as stated above, and selecting a desired mutant strain, creatine amidinohydrolase showing its optimum pH in the weakly acidic range was obtained from a mutant strain *Escherichia coli* JM (pUCE100TK).

*Escherichia coli* JM109 (pUCE100TK) was deposited under the terms of the Budapest Treaty with the National Institute of Bioscience and Human-Technology, Agency of Industrial Science and Technology (Higashi 1-1-3, Tsukuba-shi, Ibaragi Prefecture, Japan) under accession No. FERM BP-6580 on Nov. 24, 1998.

(4) Production and Purification of Creatine Amidinohydrolase The mutant strain *Escherichia coli* JM109 (pUCE100TK) obtained as above was subjected to a 16-hours shake culture in a Sakaguchi flask, which contains 100 ml of TY medium (1% bacto-tryptone, 0.5% bacto-yeast extract, 0.5% NaCl, pH7.5) containing 1 mM isopropyl-β-D-galactoside, and then was inoculated into 20L of TY medium in a 30L fermentor, the medium being prepared in the same way as above. After inoculation, the culture was carried out at 37° C. at 450 rpm for about 20 hours under aeration of 20L/min.

After culture, cells were separated from 20L of the cultured medium, using Microza (Asahi Chemical Industry Co., Ltd., Osaka, Japan, PW-303), washed with 20 mM phosphate buffer (pH7.5), and suspended in about 10L of the same buffer.

Step 1. (Preparation of Crude Enzyme Solution)

20 g of lysozyme (in 50 mM phosphate buffer, pH7.5, 100 ml) and 0.55M EDTA (pH8.0, 1L) were added to the above suspension of cells (10L), and left at 30° C. overnight. Then, 500 ml of 5% protamine solution in water (pH8.0) was added dropwise to the mixture, while stirring, to remove nucleic acids. The obtained solution was dialyzed against 10 mM CAPS-NaOH buffer (pH10.0) (hereinafter referred as buffer A).

Step 2. (DEAE-cellulose Treatment)

After about 3.0 kg (by wet weight) of DEAE-cellulose was added to about 28L of the dialysate from step 1 and mixed to absorb creatine amidinohydrolase, the DEAE-cellulose was washed with buffer A containing 5% glycerine and 0.05% 2-mercaptoethanol. Then, creatine amidinohydrolase was eluted with buffer A containing 0.5M KCl, and was concentrated by ultrafiltration.

Step 3. (DEAE-Sepharose CL-4B Treatment)

About 1.0 kg (by wet weight) of DEAE-Sepharose CL-4B bufferized with buffer A was added to about 1.0L of the concentrate from step 2 and mixed to absorb creatine amidinohydrolase, and then the DEAE-Sepharose CL-4B was washed with buffer A containing 0.05M KCl. Then, creatine amidinohydrolase was eluted with buffer A containing 0.1M KCl, and was concentrated by ultrafiltration.

Step 4. (Sephacryl S-200 Treatment)

The concentrate from step 3 (about 1.0 L) was moleculer sieved on Sephacryl S-200 filled in a column, and 2.2 g of active fraction was collected. The specific activity of the active fraction was 9U/OD280 nm. Furthermore, the properties of the obtained creatine amidinohydrolase were the same as described above.

INDUSTRIAL APPLICABILITY

According to the present invention, a creatine amidinohydrolase, in particular creatine amidinohydrolase having an optimum pH in the weakly acidic range, can be effectively produced. Therefore, the present invention is industrially usefuil in that it can provide a mensuration insusceptible to bilirubin when measuring creatinine.

It should be understood to those skilled in the art that, while the present invention is limited to the scope recited in the appended claims, various modifications or variations can be made within the scope of equivalents of the present invention. Thus, the present invention is also intended to include such modifications or variations. Furthermore, all publications, patents and patent applications cited herein are incorporated herein by reference in their entirety.

What is claimed is:

1. A creatine amidinohydrolase having the following physicochemical properties:
   (a) hydrolyzing 1 mole of creatine to generate 1 mole of sarcosine and 1 mole of urea;
   (b) having a substrate specificity to creatine;
   (c) having an optimum pH ranging from 6.0 to 7.0;
   (d) having a stable pH ranging from 4.0 to 11.0;
   (e) having an optimum temperature ranging from 50 to 55° C.; and
   (f) having a molecular weight of 92,000 Da as measured by gel filtration.

2. The creatine amidinohvdrolase according to claim 1, which is a mutant of creatine amidinohydrolase of Alcaligenes.

3. The creatine amidinohydrolase according to claim 2, which has an amino acid sequence comprising one or more mutation relative to the amino acid sequences shown in SEQ ID NO: 1.

4. The creatine amidinohydroalse according to claim 3, which is obtainable from an *Escherichia coli* strain, FERM, BP-6580.

5. A method for producing a creatine amidinohydrolase, which comprises:
   culturing a microorganism having an ability to produce the creatine amidinohydroalse according to claim 1; and recovering the creatine amidinohydrolase from the obtained culture.

6. The method according to claim 5, wherein said microorganism is *Escherichia coli* strain, FERM, BP-6580, or a strain derived from said *Escherichia coli* strain.

* * * * *

UNITED STATES PATENT AND TRADEMARK OFFICE
CERTIFICATE OF CORRECTION

PATENT NO. : 6,699,700 B1
DATED : March 2, 2004
INVENTOR(S) : Keisuke Furukawa et al.

It is certified that error appears in the above-identified patent and that said Letters Patent is hereby corrected as shown below:

Title page,
Item [54], Title, "PROCESS" should read -- METHOD --.

Column 9,
Line 47, "amidinohvdrolase" should read -- amidinohydrolase --.
Lines 48-49, "Alcaligenes." should read -- *Alcaligenes.* --.

Column 10,
Line 36, "amidinohydroalse" should read -- amidinohydrolase --.
Line 43, "amidinohydroalse" should read -- amidinohydrolase --.

Signed and Sealed this

Twenty-second Day of June, 2004

JON W. DUDAS
*Acting Director of the United States Patent and Trademark Office*

SEQUENCE LISTING

```
<160> NUMBER OF SEQ ID NOS: 1

<210> SEQ ID NO 1
<211> LENGTH: 404
<212> TYPE: PRT
<213> ORGANISM: Alcaligenes sp.

<400> SEQUENCE: 1

Met Thr Asp Asp Met Leu His Val Met Lys Trp His Asn Gly Glu Lys
 1               5                   10                  15

Asp Tyr Ser Pro Phe Ser Asp Ala Glu Met Thr Arg Arg Gln Asn Asp
                20                  25                  30

Val Arg Gly Trp Met Ala Lys Asn Asn Val Asp Ala Ala Leu Phe Thr
            35                  40                  45

Ser Tyr His Cys Ile Asn Tyr Tyr Ser Gly Trp Leu Tyr Cys Tyr Phe
        50                  55                  60

Gly Arg Lys Tyr Gly Met Val Ile Asp His Asn Asn Ala Thr Thr Ile
65                  70                  75                  80

Ser Ala Gly Ile Asp Gly Gly Gln Pro Trp Arg Arg Ser Phe Gly Asp
                85                  90                  95

Asn Ile Thr Tyr Thr Asp Trp Arg Arg Asp Asn Phe Tyr Arg Ala Val
               100                 105                 110

Arg Gln Leu Thr Thr Gly Ala Lys Arg Ile Gly Ile Glu Phe Asp His
           115                 120                 125

Val Asn Leu Asp Phe Arg Arg Gln Leu Glu Glu Ala Leu Pro Gly Val
       130                 135                 140

Glu Phe Val Asp Ile Ser Gln Pro Ser Met Trp Met Arg Thr Ile Lys
145                 150                 155                 160

Ser Leu Glu Glu Gln Lys Leu Ile Arg Glu Gly Ala Arg Val Cys Asp
               165                 170                 175

Val Gly Gly Ala Ala Cys Ala Ala Ala Ile Lys Ala Gly Val Pro Glu
           180                 185                 190

His Glu Val Ala Ile Ala Thr Thr Asn Ala Met Ile Arg Glu Ile Ala
       195                 200                 205

Lys Ser Phe Pro Phe Val Glu Leu Met Asp Thr Trp Thr Trp Phe Gln
       210                 215                 220
```

```
-continued

Ser Gly Ile Asn Thr Asp Gly Ala His Asn Pro Val Thr Asn Arg Ile
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Cys Asp His Val Asp
            260                 265                 270

Asp Ala Ser Leu Asp Ile Trp Glu Lys Asn Val Ala Val His Arg Arg
        275                 280                 285

Gly Leu Glu Leu Ile Lys Pro Gly Ala Arg Cys Lys Asp Ile Ala Ile
    290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Cys His Tyr Tyr Gly Arg
                325                 330                 335

Glu Ala Gly Val Glu Leu Arg Glu Asp Ile Asp Thr Glu Leu Lys Pro
            340                 345                 350

Gly Met Val Val Ser Met Glu Pro Met Val Met Leu Pro Glu Gly Met
        355                 360                 365

Pro Gly Ala Gly Gly Tyr Arg Glu His Asp Ile Leu Ile Val Gly Glu
    370                 375                 380

Asp Gly Ala Glu Asn Ile Thr Gly Phe Pro Phe Gly Pro Glu His Asn
385                 390                 395                 400

Ile Ile Arg Asn
```